(12) United States Patent
Brandon et al.

(10) Patent No.: US 6,648,838 B1
(45) Date of Patent: Nov. 18, 2003

(54) POSTURAL AWARENESS APPARATUS

(76) Inventors: Lee Brandon, 1444 S. Saltair Ave. #305, Los Angeles, CA (US) 90025; Michael M. Gerardi, 412 N. Oakhurst Dr. #202, Beverly Hills, CA (US) 90210; Elizabeth M. Wojciechowski, 1444 S. Saltair Ave. #305, Los Angeles, CA (US) 90025

( * ) Notice: Subject to any disclaimer, the term of this patent is extended or adjusted under 35 U.S.C. 154(b) by 0 days.

(21) Appl. No.: 09/553,564

(22) Filed: Apr. 20, 2000

Related U.S. Application Data

(63) Continuation-in-part of application No. 09/416,160, filed on Oct. 11, 1999, which is a continuation of application No. 09/023,038, filed on Feb. 13, 1998, now Pat. No. 6,019,738.

(51) Int. Cl.$^7$ .............................................. A61B 5/103
(52) U.S. Cl. ...................... 600/587; 600/594; 128/845; 482/142; 340/573.7
(58) Field of Search .................................. 482/142, 148; 128/845; 600/587, 594; 297/284.1, 284.7; 340/573.1, 573.7; 601/49, 56–60; 5/621, 630, 636–638, 640, 922, 940

(56) References Cited

U.S. PATENT DOCUMENTS

| 4,827,763 A | * | 5/1989 | Bourland et al. ......... 361/283.1 |
| 4,895,160 A | * | 1/1990 | Reents ...................... 600/484 |
| 5,684,460 A | * | 11/1997 | Scanlon ................... 340/573.1 |

* cited by examiner

*Primary Examiner*—Danton D. DeMille
*Assistant Examiner*—Tam Nguyen
(74) *Attorney, Agent, or Firm*—Michael M. Gerardi

(57) ABSTRACT

A postural awareness apparatus includes a pad, signal means for producing a signal, detection means for determining a weight applied to the pad and activating the signal means when the weight exceeds a predetermined weight, means for producing an output when the detection means determines the weight, and means for recording the output.

15 Claims, 9 Drawing Sheets

POSTURAL AWARENESS APPARATUS

This is a continuation-in-part of U.S. patent application Ser. No. 09/416,160, filed Oct. 11, 1999, which in turn is a continuation of U.S. patent application Ser. No. 09/023,038, filed Feb. 13, 1998, now U.S. Pat. No. 6,019,738, both of which are incorporated in their entireties herein by reference.

FIELD OF THE INVENTION

The present invention relates to devices for strengthening the lower back, low abdomen and posture on multiple planes, and for teaching a neutral spine.

BACKGROUND OF THE INVENTION

Devices for monitoring, controlling and correcting posture are described, for example, in U.S. Pat. No. 3,582,935, to Verhaeghe; U.S. Pat. No. 3,981,032, to Brooks; U.S. Pat. No. 4,730,625, to Fraser et al.; U.S. Pat. No. 5,146,929, to Sawhill; U.S. Pat. No. 5,279,310, to Hsien; and U.S. Pat. No. 5,522,401, to Brucker. However, such corrective devices are not designed specifically for use in strengthening the low abdomen and lower back of the user.

A need exists for an apparatus that is useful in an exercise regiment for strengthening the low abdomen and lower back of a human. A need also exists for an apparatus that informs the user when the neutral spine position is maintained while standing, sitting, driving a vehicle or during exercise in multiple positions (e.g., sitting, lying, standing).

There is also a need for an improved apparatus that can be employed to determine a user's baseline profile for use in neutral spine training and/or therapy, as well as methods of training employing such an apparatus.

SUMMARY OF THE PREFERRED EMBODIMENTS

In accordance with one aspect of the present invention, there is provided an apparatus for strengthening the abdomen and lower back of a human. The apparatus includes a pad, signal means for producing a signal, detection means for determining a weight applied to the pad and activating the signal means when the weight exceeds a predetermined weight, means for producing an output when the detection means determines the weight, and means for recording the output.

In accordance with another aspect of the present invention, there is provided an apparatus for teaching neutral spine that includes a pad, signal means for producing a signal, detection means for determining the position of at least a portion of a back of a user with respect to the pad, means for producing an output when the detection means determines that the portion of the user's back is in a preselected position with respect to the pad, and means for recording the output.

More specific embodiments of the foregoing apparatus include a processor in communication with the output producing means to receive the output, and an output device, such as a floppy disk drive, monitor or printer, in communication with the processor.

In accordance with still another aspect of the present invention, there is provided a system for use in teaching neutral spine to a passenger in a vehicle. The system includes a seat including an upright portion and a cushion portion, and signal means for producing a signal. The upright portion of the seat is adapted to contact at least a portion of a back of a user, and includes detection means for determining the position of at least a portion of a back of the user with respect to the upright portion. The signal means are activated with the detection means determines that the portion of the user's back is in a preselected position with respect to the upright portion.

In preferred embodiments, the signal means are incorporated within the upright portion of the seat. In such embodiments, preferred signal means include one-or-more vibrating units.

In other preferred embodiments, the system is mounted within a vehicle including at least one element selected from the group consisting of a sound system, a powered window, a horn, a light and an air conditioner. In these embodiments, the signal means produce a signal that activates the element (e.g., turns the sound system on).

According to still another aspect of the present invention, there is provided a postural awareness apparatus that includes a pad, signal means for producing a signal, detection means for detecting a weight applied to the pad and activating the signal means when the weight exceeds a predetermined weight, and sensor means for determining at least one physiological state of a user and producing an output indicative of the state.

In more specific embodiments, the physiological state is selected from the group consisting of heart rate, breathing rate, blood pressure and temperature.

In accordance with yet another aspect of the present invention, methods of strengthening the abdomen and lower back of a human are provided. A first method includes the steps of: contacting the back of a person to be strengthened to an apparatus that includes a pad having a longitudinal axis, proximal and distal ends and an upper surface, a head rest adjustably affixed to the proximal end of the pad, at least one vibrating unit affixed to the pad, the vibrating unit being in spaced relationship to the head rest, and detection means for detecting a weight applied to the pad and activating the signal means when the weight is less than a predetermined weight, the detection means and the signal means being affixed to the pad adjacent each other; adjusting the position of the head rest on the pad to align the head rest with the neck of the person to be strengthened and simultaneously align the at least one vibrating unit and the detection means with the lumbar region of the person to be strengthened; compressing the lumbar region of the person to be strengthened to contact the detection means, whereby the detection means in response to the compression activates the at least one vibrating unit; and compressing and relaxing the abdomen of the person to be strengthened while maintaining compression of the lumbar region of the person to be strengthened, whereby the at least one vibrating unit continues to vibrate throughout the abdominal compression and relaxation.

A second method includes the steps of: contacting the back of a person to be strengthened to an apparatus including a pad, signal means for producing a signal, and detection means for determining a weight applied to the pad and activating the signal means when the weight exceeds a predetermined weight; compressing the lumbar region of the person to be strengthened to contact the detection means, whereby a weight is applied to the pad, and compressing and relaxing the abdomen of the person to be strengthened while maintaining compression of the lumbar region; determining the weight applied to the pad as a result of the contact and producing an output corresponding to the weight; and recording the output.

In more specific embodiments, the method further includes the steps of transmitting the output to a processor, and converting the output to a human-readable or machine-readable form using the processor.

A third method includes the steps of: providing an apparatus including a pad, signal means for producing a signal, and detection means for determining a weight applied to the pad and activating the signal means when the weight exceeds a predetermined weight, the detection means including (1) means for selectably specifying the predetermined weight, (2) a counter, and (3) means for selectably specifying a maximum counter value; initializing the apparatus by specifying the predetermined weight and maximum counter value and setting the counter to an initial value; contacting the back of the user to the apparatus whereby a weight is applied to the pad; compressing the lumbar region of the person to be strengthened to contact the detection means, whereby a weight is applied to the pad, and compressing and relaxing the abdomen of the person to be strengthened while maintaining compression of the lumbar region; determining the weight applied to the pad as a result of the contact and producing a first output corresponding to the weight; transmitting the first output to a processor; processing the first output to compare the weight applied to the pad with the predetermined weight; increasing the value of the counter when the weight at least equals the predetermined weight; and increasing at least one of the predetermined weight and the maximum counter value when the counter value equals the maximum counter value.

A fourth method includes the steps of: providing an apparatus including a pad, signal means for producing a signal, and detection means for determining a weight applied to the pad and activating the signal means when the weight exceeds a predetermined weight, the detection means including (1) means for selectably specifying the predetermined weight, (2) a counter, and (3) means for selectably specifying a maximum counter value; initializing the apparatus by specifying the predetermined weight and maximum counter value and setting the counter to an initial value; contacting the back of the user to the apparatus whereby a weight is applied to the pad; determining the weight applied to the pad as a result of the contact and producing a first output corresponding to the weight; transmitting the first output to a processor; converting the first output to a human-readable form using the processor and transmitting the converted first output to an output device; observing the output device to determine whether the weight applied to the pad at least equals the predetermined weight; and advising the user to alter the user's contact with the apparatus when the weight applied to the pad is less than the predetermined weight.

In particular embodiments, the foregoing methods are practiced using specific embodiments of the inventive apparatus, including without limitation a mat, an automobile seat, an aircraft seat, a wheelchair, etc.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

The present invention provides devices and methods for strengthening the lower back and low abdomen, in particular through the technique of cocontraction, and for teaching the user to determine and maintain a neutral spine.

As used herein, "cocontraction" is defined as a simultaneous and coordinated contraction of the spine stabilizers and abdominal musculature.

"Neutral spine" as used herein denotes a biomechanically correct spinal position in which muscular balance is maintained. In neutral spine, the individual user attains a position in which the user's head, cervical, thoracic and lumbar spine are neither in flexion nor in extension. In neutral spine, the alignment of the spine is such as to optimize the tolerance of mechanical forces, including forces that occur during positioning such as sitting or standing ("static" conditions), during major movements such as rising, reclining, or entering or leaving a vehicle ("dynamic" conditions), and during movements requiring the exertion of a force, such as lifting, climbing, and the like.

Neutral spine positions vary with the posture of the user. For example, a slightly flexed neutral position ("flexion bias") occurs in a person having spondylolisthesis (a condition in the posterior portion of the spinal column). An extended neutral position ("extension bias") occurs in a person suffering from a herniated disc. Persons suffering from kyphosis will have another type of neutral position bias. Most individuals have a neutral position that is neither flexion- nor extension-biased.

Figure 1A:
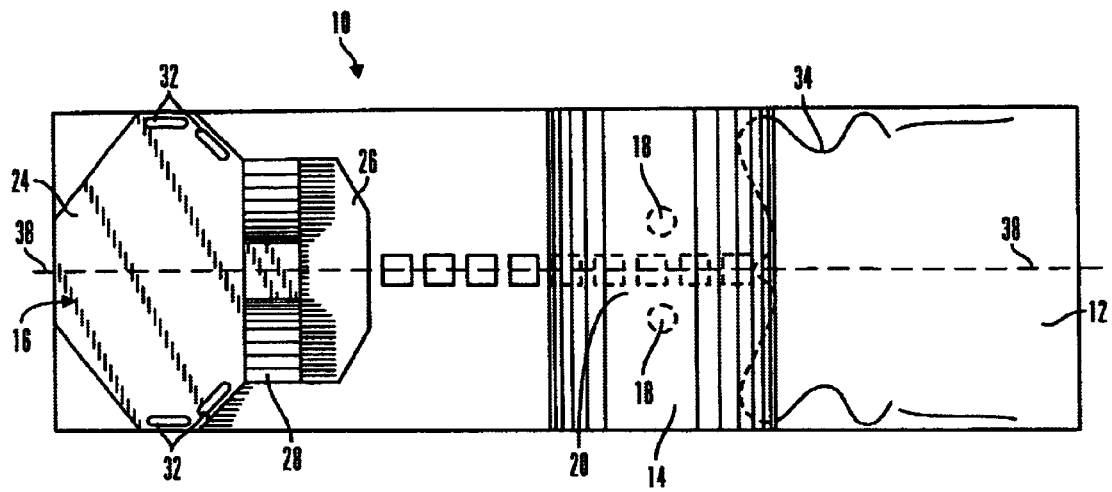
FIGS. 1a–b are top plan and exploded side views, respectively, of a first embodiment employing a detachable head rest and a lumbar pad, with vibrator units and pressure sensors disposed within the lumbar unit shown in phantom.
Figure 1B:
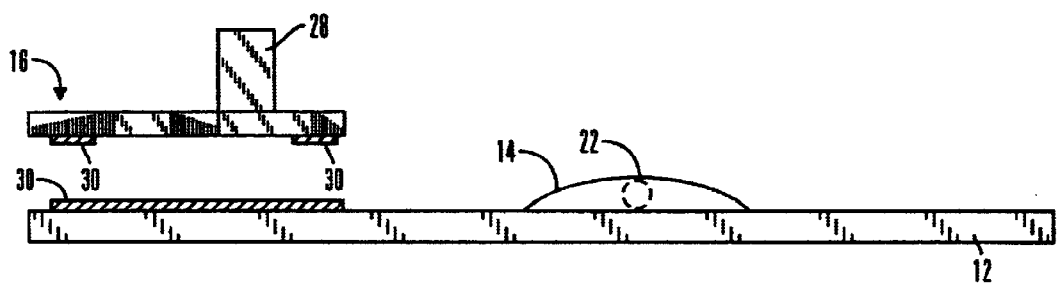
Figure 2A:
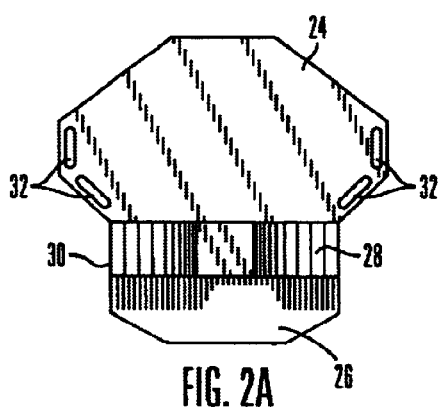
FIGS. 2a–c are top, side and end views of a detachable head rest employed with the embodiments of FIGS. 1a–b.
Figure 2B:
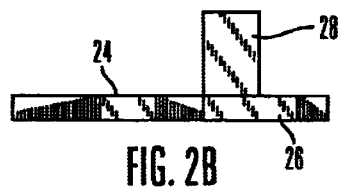
Figure 2C:
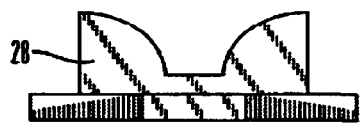
Figure 3:
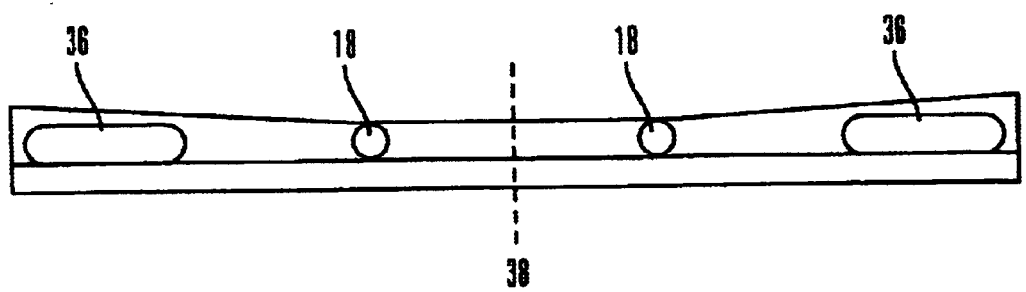
FIG. 3 is a sectional view of the lumbar pad of FIGS. 1a–b showing the location of pressure sensors and vibrator units within the pad.

Turning now to the figures, in FIGS. 1–3, a first embodiment of an apparatus 10 of the invention includes a mat 12, preferably comprised of a non-slip material, with a lumbar pad 14 and a head/neck/upper back support 16.

Lumbar pad 14 preferably is unitary with mat 12, that is, is formed from a section of mat 12. Disposed within lumbar pad 14 are means 18 for detecting a weight applied to a surface 20 of lumbar pad 14. The weight detecting means 18 can include means such as one or more mechanical switches, one or more pressure sensors, or other means known to those skilled in the art for detecting a weight applied to a surface.

The weight detecting means 18 are connected to one or more means 22 for producing a signal. The signal means 22 are activated when the selected weight detecting means 18 detect a weight applied to the surface 20 of mat 12. Once activated, the signal means 22 produce a signal that is perceptible by a person using the inventive apparatus.

Exemplary signal means 22 include, without limitation, devices for producing a vibratory signal, such as a mechanical vibrator; devices for producing an auditory signal, such as an electronic tone generator; devices for producing a visible signal, such as a light bulb or a light-emitting diode (LED); and the like, as well as combinations of such devices. The signal means 22 can be affixed to or within the apparatus 10, for example within lumbar pad 14, or can be located externally. The detection means 18 and the signal means 22 are connected together, for example as parts of an electrical circuit, or by means such as low power radio transmitters. Any means for enabling detection means 18 to activate signal means 22 are considered to be within the scope of the present invention.

Optionally, lumbar pad 14 can accommodate one or more lordosis inserts 14a disposed above detection means 18 in order to support users having excessive lordotic away. Lumbar pad 14 can also optionally include a switch (not shown) for disabling signal means 22 to allow use of the apparatus without generation of a signal.

Head/neck/upper back support 16 includes a head/neck base 24 and a cervico-thoracic support 26. A neck support 28, which optionally is adjustable in width, is disposed on head/neck/upper back support 16 between head/neck base 24 and cervico-thoracic support 26. As illustrated in FIG. 1b, head/neck/upper back support 16 is detachably affixed to mat 12 by attachment means 30, for example hook/loop devices such as Velcro® fasteners, snaps, etc., in order to allow selectable positioning of the head/neck/upper back support 16, and also to allow head/neck/upper back support 16 to be used separately if desired. In the alternative, head/neck/upper back support 16 can be permanently affixed to mat 12.

In a preferred embodiment, head/neck/upper back support 16 is provided with a plurality of handles 32. Handles 32 can be formed by cutting openings in base 24, for example, or can be separately formed and affixed to base 24.

If desired, mat surface 20 can be provided with graphics 34, such as a stylized representation of a human pelvis and lower backbone, in order to facilitate orientation of a user with respect to the mat surface. Illustrations of the positions of TLC pressure points and the locations of the detection means 18 are also beneficial to assist the user in properly orientation with respect to the apparatus 10.

In a preferred embodiment illustrated in FIG. 3, signal means 22 include two vibrators 36 disposed within lumbar pad 14 along either side of the longitudinal axis 38 of mat 12. Vibrators 36 are connected to detection means 18 and are activated when detection means 18 detect a weight (e.g., the weight of a user's body) applied to the surface 20 of mat 12.

Figure 6A:
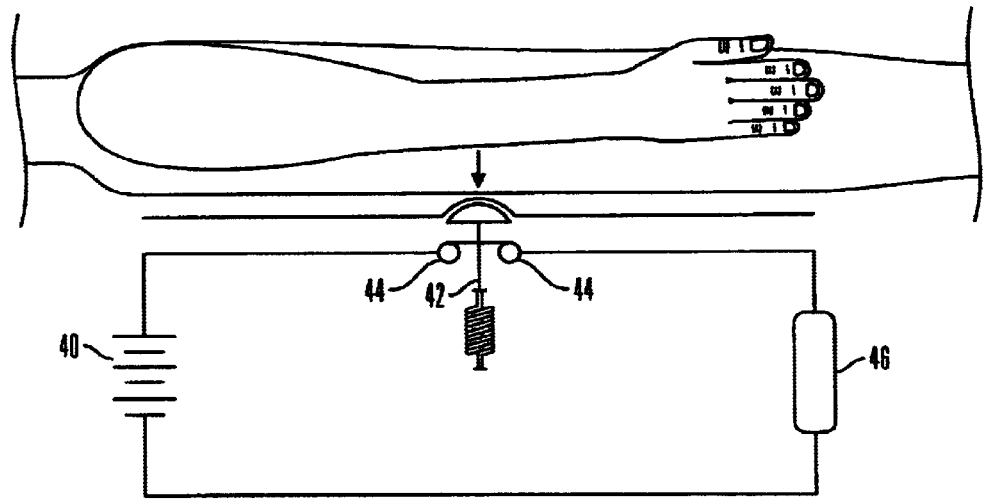
FIGS. 6a–b are schematic diagrams showing a mechanical switch useful as a pressure sensor, showing activated and inactivated states.
Figure 6B:
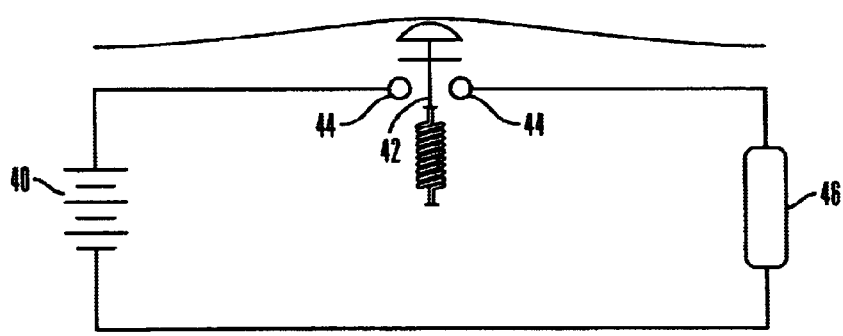

An example of detection means 18, illustrated in FIGS. 6a–b, include a power source 40, which can be a battery disposed, for example, within lumbar support 14 or at another location within, on or external to apparatus 10, or A/C power supplied via a plug; a mechanical switch 42 energized by a spring having a preselected spring constant; and a pair of contacts 44, which with signal means 22, such as a vibrator, form a circuit. In FIG. 6a, a weight, for example the weight of a user's body (indicated by a downward arrow), exceeds the spring force and causes the mechanical switch 42 to close, closing the circuit and activating signal means 22. Thus, when the user remains in contact with detection means 18, the circuit remains closed and the signal means 22 remains activated. When the signal means includes a vibrator unit 46 (shown in FIGS. 6a–b), the user perceives a vibratory signal applied to his back; in the alternative, when the signal means 22 includes a tone generator, light bulb, or LED, the user hears and/or sees the signal generated by the signal means 22. In any event, the user is informed when his low back is in contact with the detection means 18 and exerts sufficient downward force to cause switch 42 to close.

An alternative embodiment of detection means 18 includes a pressure sensor and an associated electronic circuit in place of the mechanical switch. Such accompanying circuits are readily produced by those skilled in the art to generate an output signal in response to application of a predetermined pressure to the pressure sensor. This output signal in turn activates signal means 22. Detection means 18 can also include means for measuring the weight (or force) exerted by the thoraco-lumbar area of the user.

Figure 7:
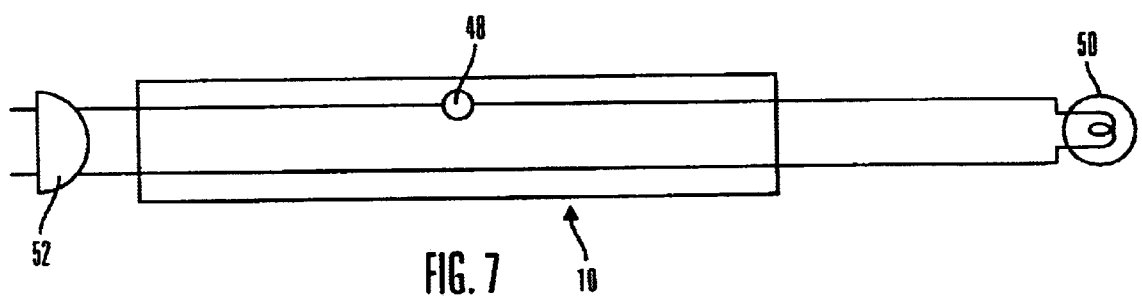
FIG. 7 is a schematic diagram of a pressure sensor with light-generating signal means and an external power supply.

FIG. 7 illustrates another embodiment of the inventive apparatus in which a pressure sensor 48 is employed rather than a mechanical switch. The signal means includes a light bulb 50. Power is supplied from an external A/C power supply via plug 52.

Optionally, a kyphosis wedge 54 is inserted between head/neck/upper back support 16 and mat 12, to accommodate users with a head forward position.

Figure 4A:
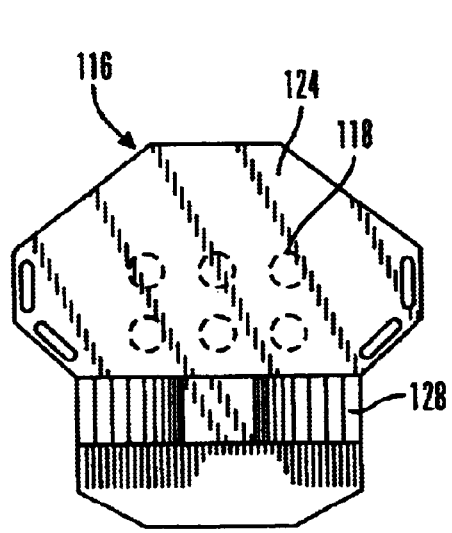
FIGS. 4a–c are top, sectional and side views of an alternative embodiment of a head rest with separate pressure sensors, vibrator units and a control switch.
Figure 4B:
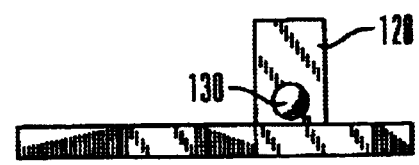
Figure 4C:
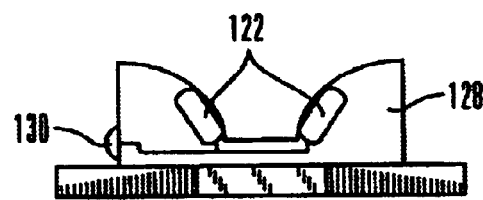
Figure 5:
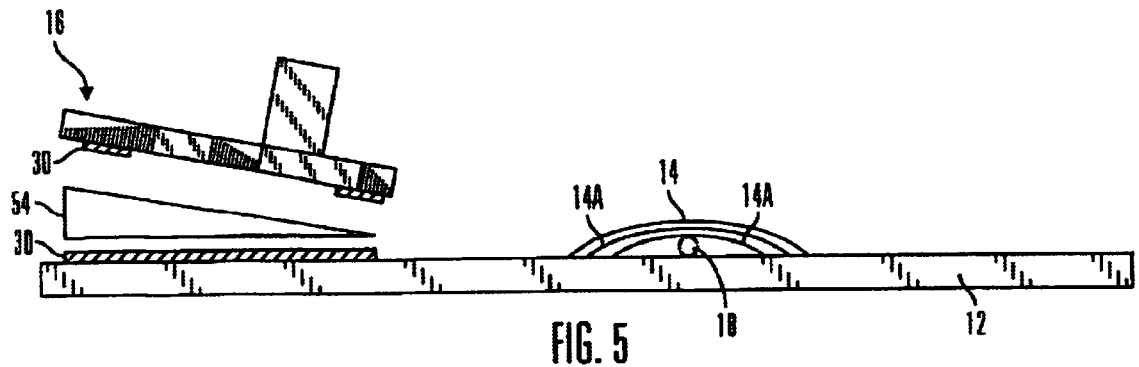
FIG. 5 is a side exploded view of an alternative embodiment including a kyphosis wedge.

FIGS. 4a–c illustrate an alternative embodiment of a head support 116 which includes detection means 118 disposed within head/neck base 124, and signal means 122. As illustrated, the signal means include one or more vibrators (for example, two pairs of vibrators) disposed within neck support 128. Detection means 118 activate the signal means 122 (e.g., vibrators) when the user's head leaves contact with detection means 118. For example, when detection means 118 includes a mechanical switch, the switch is in an open position when the user's head is in contact with it, rather than in a closed position as with detection means 18 described above. When detection means 118 includes a pressure sensor, the accompanying electronic circuit produces a signal when the pressure detected falls below a predetermined level, rather than exceeding a predetermined level.

If desired, a 3-way switch 130 can be connected to detection means 118 and the vibrators. The switch 130 allows the user to selectively enable or disable the detection means 118 and to separately control activation of the vibrators. Thus, in one position, the detection means 118 are enabled to activate the vibrators as described above with respect to detection means 18 and signal means 22. In a second position, the detection means 118 are disabled, and the vibrators are deactivated. In a third position, the detection means are disabled, and the vibrators are activated, thus allowing selective user relaxation and massage while using the inventive apparatus. According to additional specific embodiments, one or more of the vibrators can be selectively activated while the other vibrators remain inactive, thus allowing selective massage of the user's back, head, neck or combinations thereof.

Figure 8:
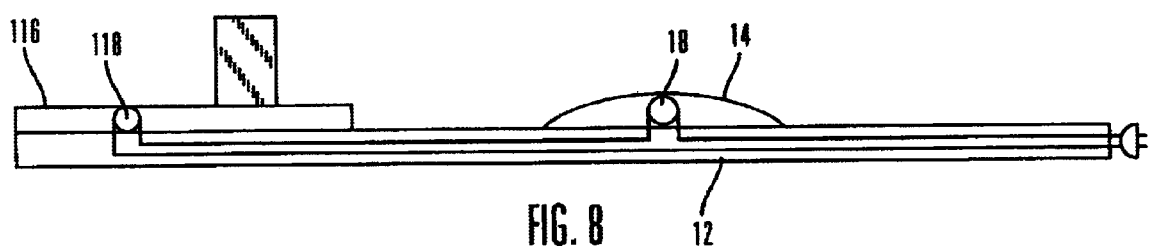
FIG. 8 is a schematic diagram of an alternative embodiment in which two pressure sensors are employed in sequence, one in the head rest and one in the lumbar pad.

The detector means 118 in the foregoing embodiment of the head support 116 can be connected in series to the detector means 18 disposed, for example, within lumbar support 14 as shown in FIG. 8. In this embodiment, the signal means 22 (and optionally vibrators disposed within head support 116) are activated only when both detector means 118 and detector means 18 detect a weight, such as the weight of a user's head and body, respectively.

The signal (vibratory, auditory, visual, etc.) provided by the inventive apparatus allows the user to heighten the intensity and tension of muscles being worked by eliminating momentum. When in use, the signal informs the user that his thoraco-lumbar area compresses the detection means 18 sufficiently to ensure the isolation of the correct muscle usage.

The inventive apparatus can be used in a variety of configurations and orientations, for example on a horizontal surface such as a floor or exercise bench. If desired, mat 12 can be provided with attachment means, such as a hook or clamp, which allows the apparatus to be affixed to a vertical surface such as a door. The apparatus can also be used on surfaces such as chairs.

The signal provided by embodiments of the inventive apparatus constitutes feedback to the user while exercising, which permits the user to minimize momentum and maximize intensity and muscular tension. To begin exercise using an embodiment of the inventive apparatus in a supine position, the belt line of the user is lined up with the low back sensors (detector means 18) in the lumbar pad 14, and the head/neck/upper back support 16 is positioned under the user's neck where it is comfortable and such that the user contacts the detector means 118 (if employed). If necessary, the position of the head/neck/upper back support 16 is adjusted to accommodate the user. In use, the low back is compressed into lumbar pad 14 by cocontraction of musculature in the low abdomen and back of the user until a signal is generated by the signal means 22. Constant tension can be maintained by cocontracting the involved muscles.

Use of the alternative embodiment of the head/neck/upper back support 116 permits the user to avoid neck flexion. If the user lifts his head during abdominal training, resulting in neck strain, the head lift is signaled to the user by the signal means 122, such as a vibration to the neck. The user can then lower his head to contact the head/neck/upper back support 116. This discourages momentum and poor form by discouraging neck flexion, or overactive arms or leg/hip flexers.

An exemplary progressive exercise routine designed specifically for embodiments of the inventive apparatus will allow the user to start with a short (e.g., 4 minute) drill series and progress at the user's own pace. Precision postural positioning for each individual user's awareness of a "neutral spine" occurs when the user re-educates the neuromuscular system using an embodiment of the inventive apparatus.

In the preceding embodiments, means 18 for detecting a weight are employed. According to further embodiments, other means can be employed to determine the position with respect to mat 14 (or another surface in which the means 18 are incorporated) of one or more portions of the user's back. Such means include, without limitation, heat sensors, infrared devices, ultrasonic devices and the like. Such alternative means are particularly useful in application where prolonged exertion of force by the user's back is not desired or is impractical (such as, for example, embodiments in which the inventive apparatus is incorporated into a vehicle seat).

Further particular embodiments of the inventive apparatus include one or more heating and/or cooling elements, in order to provide local application of heat and/or cold to one or more portions of the back of the user.

The invention has been illustrated herein as a self-contained apparatus. However, the invention can also be incorporated into another object, including without limitation objects such as an exercise apparatus (e.g., an inclined rowing machine), an exercise bench, a chair, a wheelchair, an automobile seat, an aircraft seat, a bed, etc. The invention can also be separately produced and subsequently incorporated into or affixed to another object.

Figure 9:
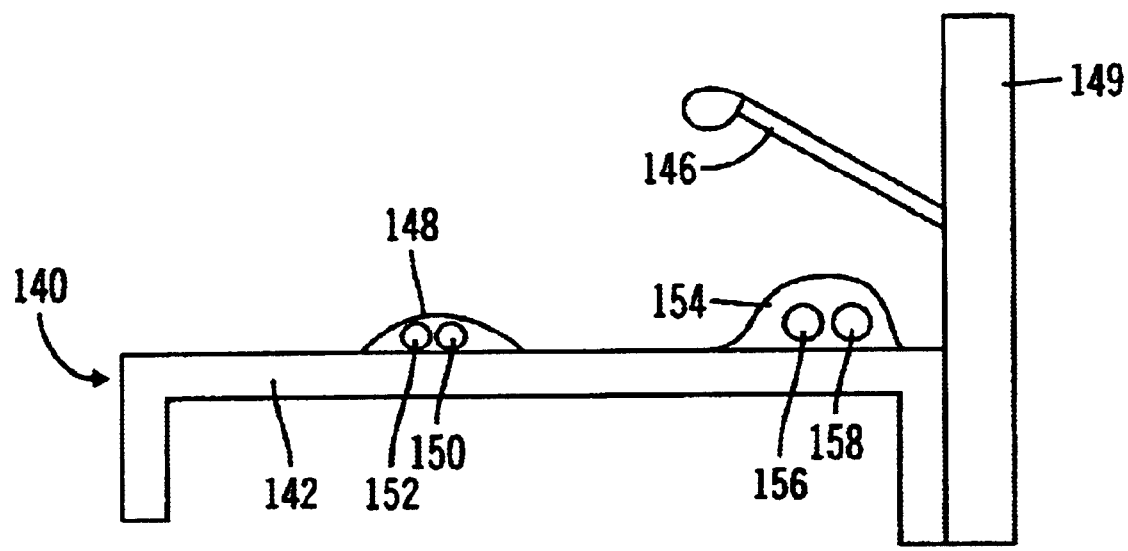
FIG. 9 is a side view of an exemplary exercise apparatus according to the invention.

Turning again to the figures, FIG. 9 illustrates an exemplary exercise apparatus 140, useful for bench presses or other similar exercises, which includes an embodiment of a postural awareness apparatus according to the invention. The embodiment of the postural awareness apparatus can be detachably secured to the bench, or can be an integral portion of the bench. Alternatively, elements of the apparatus, such as the head/neck/upper back support, can be detachably secured to the bench at either end of the bench, while the remaining elements of the apparatus are integral portions of the bench.

Apparatus 140 includes a bench 142, a weight rack 149 and a handle 146 which can be raised by a user lying on bench 142 in order to lift one or more weights (not shown). Bench 142 includes a pad portion 148 within which are disposed signal means 150 and detection means 152 as described in connection with the previous embodiments. Preferably, signal means 150 and detection means 152 are disposed in a portion of the pad portion 148 which is contacted by at least a portion of the back, preferably at least the lumbar region of the back, of the user when the user is properly positioned atop bench 142. Contact between the user's back and the detection means 152 activates the signal means when the applied weight exceeds the predetermined weight, as discussed previously.

More specific embodiments also include a head/neck/upper back support 154 with signal means 156 and detection means 158 as described above in connection with the previous embodiments. The head/neck/upper back support 154 can be detachably secured to the bench portion 142, or can be integral with the pad or unitary with the pad portion 148, as mentioned above.

Additional embodiments of exercise apparatus that include postural awareness apparatus according to the invention include, without limitation, any and all range-of-movement ("selectorized" or "resistive") devices, such as butterfly machines, horizontal chest press machines, leg press machines, and any other type of exercise apparatus in which at least a portion of the back, preferably the lumbar portion of the back, of a user contacts a surface of the exercise apparatus, or of a bench or other support used in conjunction with the exercise apparatus and considered to be part of the exercise apparatus for the purposes of this invention, and thus can activate the detection means. Non-limiting examples include apparatus targeting the back, such as lateral pull-down, narrow pull-down, low pulley row, high pulley row, pronated pull and supinated pull; apparatus targeting the chest, such as flat bench press, inclined press, flat bench fly and decline press; apparatus targeting the shoulders, such as rear delt, shoulder press, side raise, upright row and front raise; apparatus targeting the arms, such as bicep curl, tricep extension and French press; and apparatus targeting the legs, such as hamstring curl, isolated curl, leg extension, isolated leg extension, Bulgarian step-up (on bench), and bench squat with handles. Combinations of two or more such exercise devices are also included.

Such embodiments are useful in many applications, for example, in providing head/neck/upper back support and bio-feedback with regard to neutral spine to users who perform exercises according to a regime such as Pilates® or TotalGym(TM).

Figure 10:
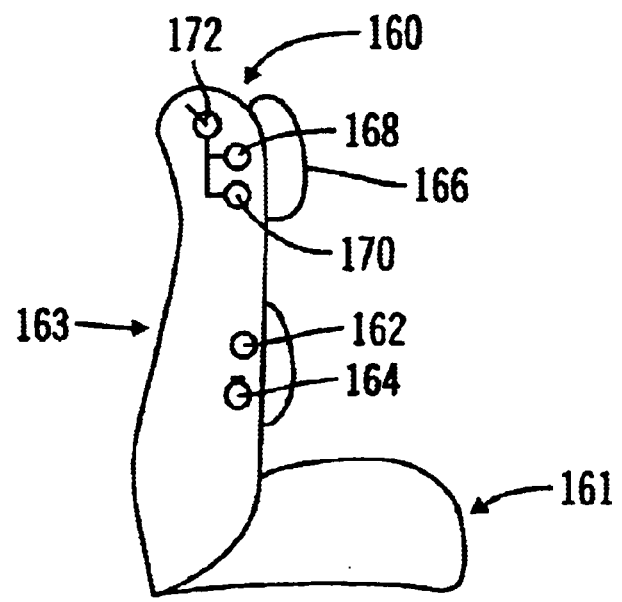
FIG. 10 is a side view of an embodiment of a seat, useful in a vehicle such as an automobile, that incorporates a postural awareness apparatus according to the invention.

In addition to exercise apparatus, embodiments of the inventive postural awareness apparatus can be affixed to or incorporated into other objects that include surfaces with which at least a portion of a user's back come into contact. FIG. 10 illustrates a seat 160 including an embodiment of the inventive postural awareness apparatus that is useful in a vehicle such as an automobile or an aircraft. Seat 160 has a cushion portion 161 and an upright portion 163 (which can be adjustable to assume inclined as well as vertical orientations). Upright portion 163 includes detection means 162, which in various particular embodiments will be weight sensors or other sensors enabling detection of the positions of one or more portions of the user's back as described above), and signal means 164, which in more specific embodiments include at least one, and preferably at least two opposed, vibrating units as discussed above. Seat 160 also includes, in more specific embodiments, a head rest portion 166 having incorporated therein second detection means 168 and second signal means 170, which preferably include one or more vibrating units, and optionally means 172 for activating the signal means 170 independently of the detection means 162, and preferably also independently of detection means 168.

In particular embodiments adapted for use in a vehicle, such as an automobile, that includes a sound system, the sound system itself can be included as a part of the signal means 164. In these embodiments, detection means 162 activates an element of the sound system, for example a radio, when it detects a weight exceeding the predetermined weight. When detection means 162 is a weight detector and the weight detected by detection means 162 falls below the predetermined weight, detection means 162 deactivates the element. For example, detection means 162 can be in electrical contact with a mute control for a car radio. When the weight applied to detection means 162 exceeds the predetermined weight, the mute control receives a signal from detection means 162 that deactivates the muting, allowing the radio to play. When the weight applied to detection means 162 falls below the predetermined weight, the mute control receives another signal that activates the muting. Similarly, when detection means 162 is a position sensor such as a heat sensor, infrared or ultrasonic device, and when the position of the appropriate portion of the user's back falls within a predetermined range, a signal is sent from means 162 to activate the element, and conversely when the user's back is outside the predetermined range.

In more specific embodiments, a control element, such as a switch, is also included that allows independent operation of the vehicle sound system, so that the user is able to operate the vehicle sound system without use of the postural awareness apparatus.

Alternatively, detection means 162 can activate the horn, lights, windows and/or air conditioner of the vehicle when the applied weight does not equal or exceed the predetermined weight. This can be achieved, for example, by inclusion of an inverter element in the apparatus and appropriate circuit elements such as a switch to enable the inverter. In such embodiments, failure of the detection means to detect sufficient applied weight can indicate that the driver has fallen asleep while at the wheel. Activation of the horn and/or air conditioner awakens the driver, while activation of the lights provides a warning to other drivers to be alert.

Further embodiments of the inventive apparatus are suitable for attachment to, or incorporation in, wheelchairs. Specific embodiments of such wheelchairs are provided with additional ballast and/or securing devices such as Velcro® straps, to enable the wheelchair's user to exercise while in the wheelchair (for example, by positioning the wheelchair adjacent to an appropriate piece of exercise equipment), and thus gain the benefits of lower back and abdominal strengthening, postural awareness and neutral spine training provided by the inventive apparatus.

In addition to facilitating the strengthening of a user's back and the teaching of neutral spine, particular embodiments of the inventive postural awareness apparatus also include additional sensor means for determining at least one physiological state of the user. Such sensor means include, without limitation, sensors for the detection of the user's heart rate, breathing rate, blood pressure and/or temperature. Any known sensors that are useful in detecting such physiological states can be employed in such embodiments.

Sensors for determining one or more physiological states of the user can be disposed in any desired portion of the embodiments of the inventive postural awareness apparatus that include them. In particular preferred embodiments, one or more such sensors are incorporated into a head rest of the inventive postural awareness apparatus, more specifically in the neck portion thereof in order to contact the skin of the user. Alternatively, the selected sensor(s) can be incorporated in separate elements such as straps, which are then secured to the user in contact with a portion of the user's skin.

The sensors for determining one or more physiological states of the user provide data to the user, or to other observers such as a trainer or a health-care professional. Preferably, the sensor data is transmitted via an electrical circuit, or by other data transmission means such as a radio or infrared device, to a microprocessor or other information processing device. Software programmed into the microprocessor then converts the raw data from the sensor(s) into a form useful to a human observer, such as a graph, plot, etc. The microprocessor then stores, records and/or displays the raw and/or processed data via one or more optional output devices such as floppy disk drives, plotters, video displays, etc. In other alternative embodiments, the sensor data is transmitted without processing to a recording or storage device for subsequent processing by means of a processor which can be part of the inventive apparatus or separate from the inventive apparatus. For example, the sensor data can be recorded on a floppy disk, or on a card having a magnetic strip. After the sensor data is stored on such a device, the data can subsequently be provided to a processor for interpretation and use. In this way, in specific embodiments, a user can exercise using two or more different embodiments of the inventive apparatus, with each embodiment generating sensor data that are sequentially recorded, e.g., on a single card carried by the user. The sensor data can be subsequently processed to generate a profile of the user's activities on each different embodiment of the inventive apparatus.

In addition to the foregoing embodiments that provide for storage of sensor data, other more specific embodiments include a transmission device which transmits the raw and/or processed data to a remote site (e.g., within a gym, at a physician's office, etc.). Such embodiments facilitate remote observation of the physiological state(s) of the user by, for example, the user's health-care professional.

Further more specific embodiments of the inventive postural awareness apparatus are capable of providing a record of the performance of the user. In such embodiments, the apparatus preferably includes a plurality of pressure sensors disposed at different locations along the pad. Each of the pressure sensors provides an output indicative of the magnitude of the pressure applied at its location. Optionally, the pressure sensors and/or additional sensors also measure further quantities such as local downward acceleration. The data provided by the pressure sensor are in turn input into a processor, at which time appropriate software convert the raw data into useful output, which can be stored, recorded and/or transmitted in any desired manner.

The data so obtained can be used, for example, to prepare a plot of the pressures, downward accelerations, etc., measured at each point versus time. Appropriate software, readily prepared by those skilled in the art, can be employed to generate plots or visual displays of the state of the user's spine during exercise, from any desired view, such as the front or side. Such plots can be employed by the user or the user's trainer to evaluate whether the user is performing a specific exercise properly. For example, exercise in accordance with correct neutral spine training will yield a plot showing that the user's lumbar region is maintained in contact with the pad and activates the appropriate sensors at all times during the exercise. Improper exercise, in contrast, will yield a plot indicative of distorted form, excessive momentum and/or other indicia that the exercise was not performed correctly. Evaluation of the downward accelerations measured at each point by the sensors will enable the user and/or the user's trainer to determine whether the exercise is performed excessively forcefully, i.e., whether the user's speed of movement is excessive or distorts form.

Data obtained over the course of several uses likewise can be evaluated to determine whether the user's exercise form is changing, in particular whether the user's form is improving over the course of training. Such evaluations can be carried out, for example, by observing whether sensors that are activated due to incorrect form during earlier uses are no longer activated during later uses.

The data obtained from the various sensors employed in the foregoing embodiments of the inventive postural awareness apparatus, in addition to being useful for evaluating the user's performance, can also be used as part of a progressive exercise regimen. In these embodiments, the detection means include pressure sensors that are individually programmable, such that the predetermined weight at which the signal means are activated can be varied. The processor applies appropriate software to track the performance of the user and to vary the predetermined weight(s) in response to the user's progress. For example, when the user has correctly performed a specific number of repetitions of an exercise, the processor instructs the pressure sensors to increase the predetermined weight by a selected increment.

Figure 11:
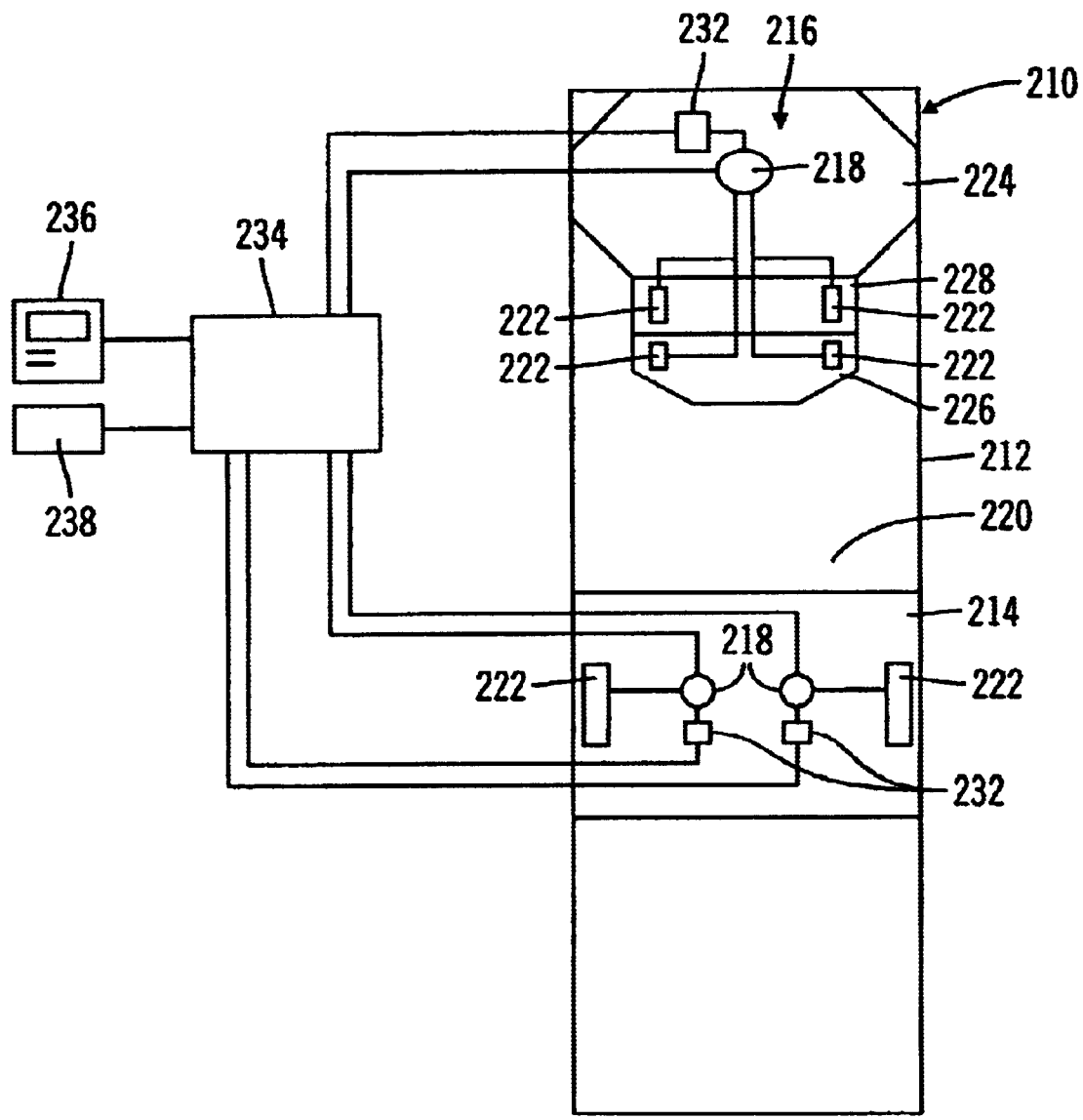
FIG. 11 is a side view of an embodiment of a postural awareness apparatus according to the invention that is useful in monitoring and/or documenting the performance of a user.

FIG. 11 illustrates an embodiment of an apparatus according to the invention that is useful in monitoring and/or documenting the performance of a user. Apparatus 210 includes a mat 212 having a portion 214 that is adapted to engage a portion of the user's back. Portion 214 can be a lumbar pad, or can be simply a portion of the mat itself; if a lumbar pad is employed, the pad can be releasably or permanently affixed to the mat 212. Apparatus 210 further includes a head/neck/upper back support 216, which in more specific embodiments includes a head/neck base 224 and a cervico-thoracic support 226. The head/neck base and cervico-thoracic support can be unitary, forming part of a single structure, or can be separate elements affixed together releasably or permanently.

Means 218 for detecting a weight applied to surface 220 of portion 214 of mat 212, and signal means 222 (e.g., vibrating units) in communication with and responsive to means 218 are disposed within apparatus 210 as a manner similar to that described above with respect to previous embodiments. Preferred embodiments of means 218 that are particularly useful in the apparatus of FIG. 11 include electronic or solid-sate pressure transducers. In particular embodiments, the pressure transducers so employed are adjustable to detect a weight having a value that is freely selectable by the user. Such selectivity can be provided by, for example, a dedicated electronic circuit 232 that is part of, or in communication with, the pressure transducer and is addressable by a human user or observer, and/or by a separate internal or external processor 234, such as an Intel Pentium® processor, with which the pressure transducer is in communication and which performs functions in addition to adjustment of the minimum weight to which the pressure transducer is responsive. Preferably a processor 234 is employed.

Very preferably the means 218 measures the weight applied thereto and provides an output indicative of the magnitude of the weight applied and of whether the weight equals or exceeds the predetermined minimum weight. Such an output can be provided by, for example, a dedicated electronic circuit (not shown) in manners well known to those skilled in the art.

In optional more specific embodiments, one or more means 218 (one is shown) and one or more signal means 222 (four are shown) can also be disposed in head/neck/upper back support 216, in a manner similar to that described in connection with preceding embodiments.

Detection means 218 and signal means 222 can be supplied with power by any conventional means, such as batteries or external AC plugs (not shown), in manners well known to those skilled in the art.

Processor 234 communicates with output device 236, such as, e.g., a video display, a disk drive, a printer, etc. In preferred embodiments, processor 234 also communicates with modem 238, in order to facilitate monitoring and control of the use of apparatus 210 via the Internet.

Alternative embodiments of the foregoing apparatus 210 include sensors other than, or in addition to, weight detectors, in manners similar to those discussed above. Such sensors include, without limitation, sensors for determining at least one physiological state of the user and sensors for determining the proximity of one or more portions of the user's back to the portion 214, such as heat sensors, infrared or ultrasonic devices.

Apparatus 210 as illustrated herein can be used in connection with numerous diagnostic, therapeutic and training methods, including without limitation methods for determining and teaching awareness of neutral spine, methods of establishing a baseline profile upon which to base corrective therapies, and methods for strengthening the abdomen and lower back of a human user.

In an exemplary method for determining the baseline profile of a user employing an embodiment of the inventive apparatus, a user assumes a position (e.g., supine or standing in an upright or flexed position) such that at least a portion of the user's back is in contact with an embodiment of the inventive apparatus, and such that at least one weight sensor and/or position sensor as described above is in proximity to the portion of the user's back. The weight exerted by the user's back as measures by the weight sensor while the user assumes the selected position(s) with respect to the apparatus, or alternatively the position of the portion of the user's back with respect to the position sensor(s), is determined. On the basis of such measurements, the user's trainer or health care professional determines whether any corrective means (such as lordotic or kyphotic inserts) are required for the user to achieve neutral spine positioning. At this point, the position of the user's spine, with any necessary additional support as provided by appropriate inserts, establishes the baseline profile from which further therapy and/or training can proceed.

Figure 12:
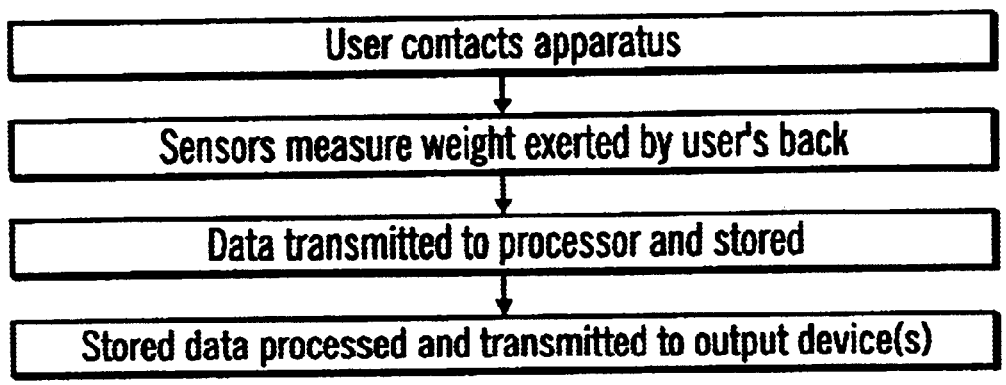
FIGS. 12–14 are flow charts illustrating exercise methods employing embodiments of the inventive postural awareness apparatus.

Turning again to the figures, FIG. 12 illustrates a first method for strengthening the abdomen and lower back of a user. According to this basic method, the user contacts the apparatus 210 in a manner as described herein, such that a portion of the user's back, more preferably a portion of the lumbar area of the user's back, contacts the corresponding portion of the surface of the pad 214 of the apparatus, within which the detection means 218 are disposed, and thereby applies a weight to the pad. Detection means 218 determines the weight applied to the surface of the pad, and provides an output indicative of the weight applied and of whether it equals or exceeds the predetermined minimum weight to processor 234. The output from detection means 218 preferably is stored and subsequently processed to convert it into a human-readable or machine-readable form, after which the processed data is transmitted to output device 236 to produce a record of the user's performance using the apparatus.

Figure 13:
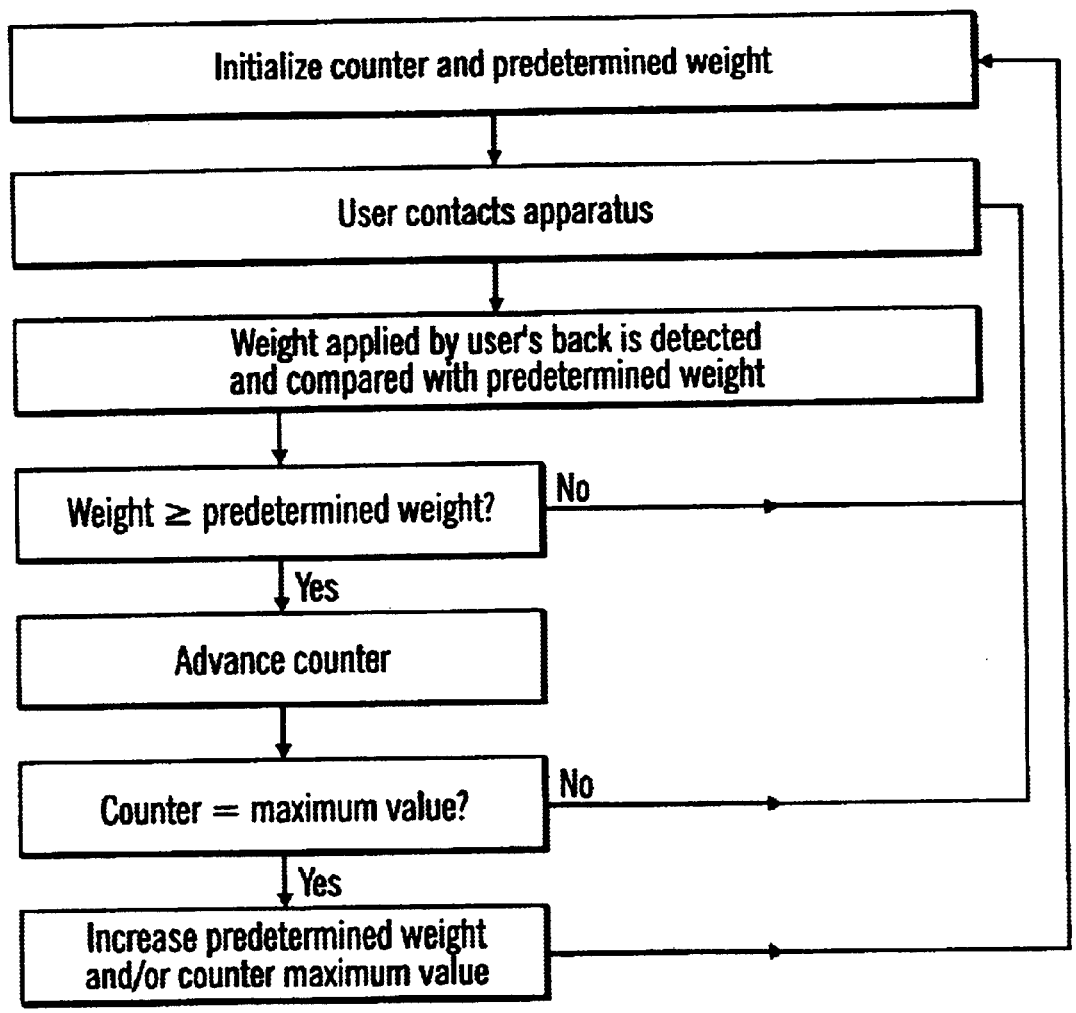

The foregoing method is particularly useful when it is not desired to actively monitor or correct the user's performance, but only to provide a record of the performance. In FIG. 13, a second method employing an embodiment of the inventive apparatus is schematically described. This method is suitable for use by a human user who desires to modify his or her performance in order to achieve perfect form during the exercise, but who does not have the direct assistance of a trainer. In this method, preferably the processor 234 is provided with appropriate software to facilitate monitoring of the number of times the user produces correct neutral spine positioning during the course of the exercise and/or the total duration of correct lumbar compression achieved during the exercise. That is, the software includes a counter that can be initialized to a selected value (e.g., zero repetitions, zero total compression time, etc.), depending on the desired measure of correct exercise performance, prior to commencement of the exercise.

According to embodiments of the second method, the user first initializes the counter to a desired value, and also specifies the initial predetermined weight to be detected by means 218, the maximum counter value, and the desired increase in the predetermined weight and/or the maximum counter value to be performed upon successful completion of the exercise. The user next contacts the apparatus 210 in the manner described herein, thereby applying a weight that is detected by means 218. The weight so applied is detected and compared with the predetermined weight. At this point, if the weight so applied is not at least equal to the predetermined weight, and therefore if no signal is generated by the signal means, the user repeats the contact. When the weight applied by the user's back equals or exceeds the predetermined weight, the counter is advanced, depending on the particular counter employed, the counter can be advanced, e.g., by one unit, by the length of time during which the predetermined weight is equaled or exceed, or by some other appropriate increment. When the counter value equals the maximum counter value, the predetermined weight and/or the maximum counter value is increased by the previously specified value(s). The user then repeats the exercise as desired.

As a first example of the foregoing method in which a specified number of repetitions of correct compressions of the lumbar region of the user's back are performed, a user initializes the counter to zero, specifies the predetermined weight, and selects a maximum counter value (e.g., ten). The user selects an increment of 5% of the initial predetermined weight and an increment of zero in the number of repetitions. After assuming a supine position upon the inventive apparatus, the user compresses his or her lumbar region, thereby applying a weight that is detected by the detection means. When the predetermined weight is applied, the counter advances by one. The user then relaxes his or her lumbar region and repeats the compression; each correct compression advances the counter one unit. Once ten correct repetitions have been performed, the predetermined weight is increased by the selected increment (here, 5%), while the number of repetitions is not increased. The user then repeats the exercise using the increased predetermined weight, and continues as desired.

As a second example, a user initializes the counter to zero seconds, specifies the predetermined weight, and selects a maximum counter value (e.g., 120 seconds). The user selects an increment of 5% of the initial predetermined weight and an increment of 60 in the number of seconds. The user compresses his or her lumbar region as described above, thereby applying a weight that is detected by the detection means. Once the predetermined weight is applied, the counter advances by the number of seconds during which the predetermined weight is applied, and thus by the time during which the exercise is correctly performed. Once the predetermined weight has been applied for 120 seconds, the predetermined weight is increased by the selected increment (here, 5%), and the counter value is increased to 180 seconds. The user then repeats the exercise using the increased predetermined weight and duration of weight application, and continues as desired.

Figure 14:
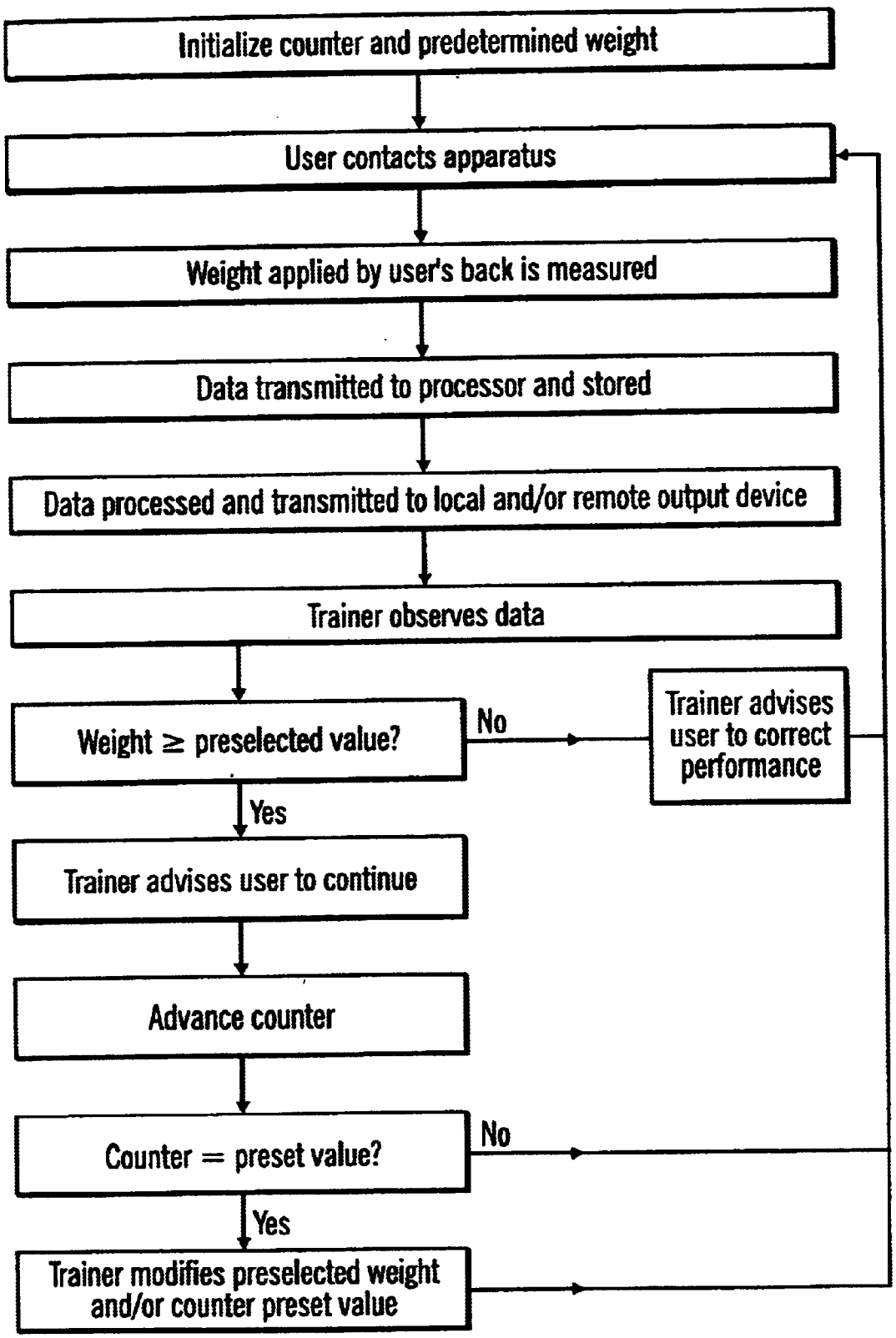

In FIG. 14, a third method employing an embodiment of the inventive apparatus is schematically described. This method is suitable for use by a human user together with a trainer or health care professional, such as a doctor, who can be present together with the human user or who can monitor and advise the user from a remote location. In this method, preferably the processor 234 is provided with appropriate software to facilitate monitoring of the number of times the user produces correct lumbar compression during the course of the exercise and/or the total duration of correct lumbar compression achieved during the exercise, as described in connection with the second method. The apparatus also is provided with an output device and/or a remote access device, for use by, e.g., the user's trainer.

According to particular embodiments of the third method, the user first initializes the counter and predetermined weight in a manner similar to that described above in connection with the second method. Alternatively, the user's trainer, health care professional, or the like, can perform the initialization, either in person or remotely, such as via an Internet connection. The user next applies a weight to the apparatus in the manner previously discussed. The weight so applied is detected by means 218 and compared with the predetermined weight, for example after transmission to and processing by the processor 234.

The processed data then is converted into a human-readable form which is observed by the user's trainer. For example, the data is displayed on a monitor when the trainer is present at the site of the exercise. Alternatively, the data is displayed at a remote site via an Internet connection. At this point, if the weight so applied is not at least equal to the predetermined weight, the user's trainer advises the user to correct his or her performance of the exercise. When the user correctly performs the exercise, such that the weight applied by the user's back equals or exceeds the predetermined weight, the trainer observes the data indicative of correct performance and advises the user to continue. The counter is advanced in the manner described in connection with the second method, until the counter value equals the maximum counter value. When the counter value equals the maximum counter value, the user's trainer changes the predetermined weight and/or the maximum counter value by an appropriate increment as selected by the trainer. The user then repeats the exercise as desired.

What is claimed is:

1. An apparatus for teaching neutral spine comprising
   a) a pad,
   b) signal means for producing a signal,
   c) detection means for determining the position of at least a portion of a back of a user with respect to said pad,
   d) means for producing an output when said detection means determines that said portion of said back is in a preselected position with respect to said pad, and
   e) means for recording said output.

2. The apparatus of claim 1 further comprising
   f) a processor in communication with said means (d) to receive said output, and
   g) an output device in communication with said processor (e).

3. The apparatus of claim 1 wherein said detection means c) is a weight sensor that detects a weight applied to said pad and activates said signal means when said weight exceeds a predetermined weight, whereby said weight applied to said pad provides an indication of the position of said portion of said back with respect to said pad.

4. The apparatus of claim 1 wherein said detection means c) is a heat sensor that is activated when said sensor detects a temperature produced by contact with said portion of said back that exceeds a predetermined temperature.

5. A postural awareness apparatus comprising
   a) a pad,
   b) signal means for producing a signal,
   c) detection means for detecting a weight applied to said pad and activating said signal means when said weight exceeds a predetermined weight, and
   d) sensor means for determining at least one physiological state of a user and producing an output indicative of said state.

6. The postural awareness apparatus of claim 5 wherein said physiological state is selected from the group consisting of heart rate, breathing rate, blood pressure and temperature.

7. The apparatus of claim 5 wherein said signal means produces a signal selected from the group consisting of a vibratory signal, an auditory signal and a visible signal.

8. The apparatus of claim 7 wherein said signal means comprises at least one vibrator unit.

9. The apparatus of claim 5 further comprising a head rest affixed to said pad.

10. The apparatus of claim 9 wherein said head rest comprises at least one vibrator unit disposed within said head rest.

11. The apparatus of claim 10 further comprising means for activating said at least one vibrator unit disposed within said head rest independent of said detection means.

12. The apparatus of claim 5 wherein said detection means comprises a pressure sensor and an electronic circuit which generates an output when pressure measured by said pressure sensor exceeds a predetermined pressure.

13. The apparatus of claim 9 wherein said head rest comprises second detector means for detecting a weight applied to said head rest and second signal means, said second detector means activating said second signal means when said weight is below a predetermined weight.

14. The apparatus of claim 5 wherein said detection means comprises means for measuring said weight.

15. The apparatus of claim 5 further comprising means for recording said output indicative of said state.

* * * * *

UNITED STATES PATENT AND TRADEMARK OFFICE
Certificate

Patent No. 6,648,838 B1                                                                    Patented: November 18, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Lee Brandon, Los Angeles, CA; and Elizabeth M. Wojciechowski, Los Angeles, CA.

Signed and Sealed this Thirteenth Day of April 2004.

*NICHOLAS D. LUCCHESI*
*Supervisory Patent Examiner*
*Art Unit 3764*